(12) United States Patent
Rao

(10) Patent No.: US 6,291,729 B1
(45) Date of Patent: *Sep. 18, 2001

(54) HALOFLUOROCARBON HYDROGENOLYSIS

(75) Inventor: V. N. Mallikarjuna Rao, Wilmington, DE (US)

(73) Assignee: E. I. du Pont de Nemours and Company, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/351,908

(22) Filed: Dec. 8, 1994

(51) Int. Cl.$^7$ .................................................. C07C 17/10
(52) U.S. Cl. .............................................. 570/176
(58) Field of Search ............................................. 570/176

(56) References Cited

U.S. PATENT DOCUMENTS

| | | | |
|---|---|---|---|
| 2,942,036 | 6/1960 | Smith et al. | 260/653 |
| 4,319,060 | 3/1982 | Cunningham et al. | 570/177 |
| 4,873,381 | 10/1989 | Kellner et al. | 570/176 |
| 4,980,324 | * 12/1990 | Kellner et al. | 570/176 |
| 5,068,472 | 11/1991 | Webster et al. | 570/157 |
| 5,171,901 | 12/1992 | Gassen et al. | 570/168 |

FOREIGN PATENT DOCUMENTS

| | | |
|---|---|---|
| 2 081 813 | 5/1993 | (CA) . |
| 0 349 115 | 1/1990 | (EP) . |
| 0 442 075 | 8/1991 | (EP) . |
| 0 539 989 | 5/1993 | (EP) . |
| 1 578 933 | 11/1980 | (GB) . |
| 1-319441 | 12/1989 | (JP) . |
| WO 90/08748 | 8/1990 | (WO) . |
| WO 94/20440 | 9/1994 | (WO) . |

OTHER PUBLICATIONS

Bitner, J.L. et al, , "Thermochemical and Photochemical studies on organic fluorine compounds", *Chemical Abstracts*, 54:22311C. (1959).

Bitner, J.L. et al, *U.S. Dept. of Comm. Off. Tech. Ser./Report 136732*, , pp. 25–27 (1958).

* cited by examiner

*Primary Examiner*—Alan Siegel

(57) ABSTRACT

A highly selective process is disclosed for the hydrogenolysis of 2,2-dichlorohexafluoropropane (i.e., CFC-216aa or $CF_3CCl_2CF_3$) to 2,2-dihydrohexafluoropropane (i.e., HFC-236fa or $CF_3CH_2CF_3$) and 2-chloro-2-hydrohexafluoropropane (i.e., 226da or $CF_3CHClCF_3$). The process involves reacting the starting material with hydrogen at an elevated temperature of about 300° C. or less in the presence of a catalyst containing a catalytically effective amount of palladium supported on a support of fluorinated alumina and/or aluminum fluoride.

20 Claims, No Drawings

HALOFLUOROCARBON HYDROGENOLYSIS

FIELD OF THE INVENTION

This invention relates to catalytic hydrogenolysis of halofluorocarbons; and more particularly to the hydrogenolysis of said materials using palladium-containing catalysts.

BACKGROUND

Various processes for the catalytic hydrogenolysis of chlorofluorocarbons and hydrochlorofluorocarbons are known. For example, British Patent Specification 1,578,933 illustrates that mixtures of $C_2Cl_2F_4$ isomers can be subjected to hydrogenolysis over a particulate catalyst of palladium on charcoal (which was intimately mixed with glass helices to prevent clogging) or palladium on alumina, to mixtures of $C_2H_2F_4$ isomers. U.S. Pat. No. 2,942,036 discloses the reaction of 1,2,2-trichloropentafluoropropane with hydrogen in the presence of palladium on activated carbon catalyst to produce 1,2,2-trihydropentafluoropropane. The examples show that under the conditions of the experiments one of the products from this reaction is $CF_3CH=CF_2$. The carbon support may be treated with aqueous HF prior to depositing palladium on the support for the purpose of removing silica from the carbon. U.S. Pat. No. 5,171,901 discloses inter alia the catalytic hydrogenation of $CF_3CCl_2CF_3$ and/or $CF_3CHClCF_3$ using suitable catalysts (e.g., palladium). Disclosed support materials include activated carbons, aluminas, silicas, barium sulfate, spinels, silicates and titanium dioxide. Preferred supports are activated carbons and lithium/aluminum spinels. Examples are provided wherein 2,2,-dichlorohexafluoropropane and 2-chloro-2-hydrohexafluoropropane are hydrogenated using palladium supported on globular lithium/aluminum spinel. Japanese Patent Application Publication Hei 1(1989)-319441 discloses a process where one chlorine atom is selectively replaced by hydrogen in 1,1,1-trichlorotrifluoroethane using a platinum catalyst. For comparison, a palladium on carbon catalyst is disclosed to produce 1,1,1-trifluoroethane as the major product under the conditions of the experiment.

SUMMARY OF THE INVENTION

The present invention provides a process for the hydrogenolysis of 2,2-dichlorohexafluoropropane (i.e., CFC-216aa or $CF_3CCl_2CF_3$) to 2,2-dihydrohexafluoropropane (i.e., HFC-236fa or $CF_3CH_2CF_3$) and 2-chloro-2-hydrohexafluoropropane (i.e., 226da or $CF_3CHClCF_3$). The process comprises reacting said starting material with hydrogen at an elevated temperature of about 300° C. or less in the presence of a catalyst containing a catalytically effective amount of palladium supported on a support selected from the group consisting of fluorinated alumina, aluminum fluoride and mixtures thereof.

DETAILED DESCRIPTION

The catalysts suitable for the process of this invention comprise palladium. The palladium is supported on fluorinated alumina, aluminum fluoride and/or a mixture thereof. Preferred catalysts consist essentially of palladium on an aluminum fluoride or fluorinated alumina support. The procedure for preparing such a catalyst is described in U.S. Pat. No. 4,873,381, the entire contents of which are hereby incorporated herein by reference.

The concentration of palladium on the fluorinated alumina and/or aluminum fluoride support is typically within the range of from 0.1 to 10% by weight of the catalyst. The support can be prepared by fluorination of alumina at elevated temperatures. It is preferred that the fluorine content of the support be sufficient to provide a fluorine to aluminum atomic ratio of at least 2.4. The aluminum fluoride or fluorinated alumina support utilized in the instant invention has the advantage of being regeneratable by conventional means, which carbon-based supports do not have. For example, $CF_3CCl_2CF_3$ can be reacted with hydrogen over a catalyst of this invention until the conversion rate of CFC-216aa decreased by at least about 20 percent compared to the conversion rate of CFC-216aa using fresh catalyst at the same conditions; and the catalyst can then be regenerated (e.g., by first treating with air or oxygen at elevated temperature, and then reducing with hydrogen).

The reaction temperature is typically within the range of from about 100° C. to about 300° C. A preferred range is from about 100° C. to 250° C. Generally, in order to provide substantial hydrogenolysis product yields, the amount of hydrogen used is at least about 0.5 mole per mole of the CFC-216aa starting material. To provide yields desired in many embodiments, at least stoichiometric amounts of hydrogen are used. A considerable excess of hydrogen can also be advantageously employed to provide the yields desired in many embodiments in addition to serving as a heat sink to reduce the overall temperature rise in the reactor. The three-carbon hydrogenolysis product from the hydrogenolysis of CFC-216aa contains at least 90% of the fluorine atoms contained in the CFC-216aa reacted and less than 5 mole percent of said product contains 5 fluorine substituents.

CFC-216aa utilized in this process can be made by conventional means which are well known to the art (see, e.g., U.S. Pat. No. 5,068,472).

The hydrogenolysis of 2,2-dichlorohexafluoropropane with hydrogen may be conducted in any suitable reactor, including fixed and fluidized bed reactors. The reaction vessel should be constructed from materials which are resistant to the corrosive effects of hydrogen halide.

Pressure is not critical. Atmospheric and superatmospheric pressures are the most convenient and are therefore preferred.

Unreacted 2-chloro-2-hydrohexafluoropropane may be recycled to the reactor to produce additional quantities of 2,2-dihydrohexafluoropropane or be used as an organic intermediate to produce 2-hydroheptafluoropropane.

HFC-236fa is useful as a refrigerant, fire extinguishant, heat transfer medium, gaseous dielectric, sterilant carrier, polymerization medium, particulate removal fluid, carrier fluid, buffing abrasive agent, displacement drying agent and power cycle working fluid. In particular, HFC-236fa is a highly effective refrigerant.

The present process has the advantage that the desirable products are obtained in extremely high selectivity.

Practice of the invention will become further apparent from the following non-limiting examples.

EXAMPLES

Preparation of Palladium on Fluorinated Alumina

Commercial 0.5 weight percent palladium on alumina (21.4 g, 1.6 mm extrudates) was placed in a reactor and heated to 175° C. in a flow of nitrogen (20 cc/min.) for about 2 hours. At the end of this period the nitrogen flow was increased to 50 cc/min. and an HF flow (50 cc/min.) was passed through the reactor. After the initial exotherm subsided (about three hours), the nitrogen flow was reduced to 20 cc/min. and the HF flow increased to 80 cc/min. The reactor temperature was then gradually increased to about 400° C. over about a five hour period and maintained at 400° C. for an additional 30 minutes. The HF flow was then stopped and the reactor purged with nitrogen. The palladium on fluorinated alumina prepared by this method was used in the hydrogenolysis experiment below.

Hydrogenolysis of CFC-216aa using Palladium on Fluorinated Alumina Catalyst

Run No. 1—Liquid CFC-216aa (3 mL/hour) was vaporized and mixed with 20 cc/minute of hydrogen. This vapor mixture was sent through a 0.5" (12.7 mm) O.D.×8" (203 mm) Hastelloy™ nickel alloy reactor containing 15.5 g of the palladium on fluorinated alumina catalyst maintained at 150° C. using a fluidized sand bath. After nine hours of operation under these conditions, organic product analysis using conventional gas chromatography indicated that CFC-216aa conversion was essentially complete. The hydrogen-containing products included 32.4% HFC-236fa (2,2-dihydrohexafluoropropane) and 64.5% HCFC-226da (2-chloro-2-hydrohexafluoropropane) in addition to very small quantities of other products.

Run No. 2—Run No. 1 was repeated except that the temperature was 200° C. After about 15 hours of operation, CFC-216aa conversion was still complete. The organic hydrogen-containing products included 45.5% HFC-236fa and 52% HCFC-226da.

Run No. 3—Run No. 2 was repeated except that the hydrogen flowrate was increased to 40 cc/minute. The CFC-216aa conversion was complete. The organic hydrogen-containing products included 48.9% HFC-236fa and 49.4% HCFC-226da.

Run No. 4—Run No. 3 was repeated except that the temperature was increased to 250° C. The organic hydrogen-containing products included 64.5% HFC-236fa and 28.0% HCFC-226da.

Run No. 5—Run No. 4 was repeated except that the hydrogen flow rate was reduced to 20 cc/min. CFC-216aa conversion was complete. The organic hydrogen-containing products included 63.1% HFC-236fa and 30.1% HCFC-226da.

Comparative Hydrogenolysis of CFC-216aa using Palladium on low-ash acid-washed carbon Carbon Support The carbon support used in the examples was a 4×8 mesh (about 4.7 mm×2.4 mm) commercial grade coconut shell carbon which had (before washing) an ash content of about 2.6 weight percent. After hydrochloric acid washing, the carbon support had an ash content of less than about 0.1 weight percent.

Run No. 6—Liquid CFC-216aa (3 mL/hour) was vaporized and mixed with 10 cc/minute of hydrogen. This vapor-mixture was sent through a 0.5" (12.7 mm) O.D.×8" (203 mm) Hastelloy™ nickel alloy reactor containing 7.2 g of 0.5 weight percent palladium supported on low-ash, acid-washed carbon maintained at 150° C. using a fluidized sand bath. Organic product analysis using conventional gas chromatography indicated that about 90% of the starting material had been converted. The hydrogen-containing products included 15.7% 2,2-dihydrohexafluoropropane (HFC-236fa), 54.3% 2-chloro-2-hydrohexafluoropropane (HCFC-226da), 12.3% 2-hydropentafluoropropene, and 1.7% 1,2,2-trihydropentafluoropropane (HFC-235fa) and small quantities of other compounds.

Run No. 7—Run No. 6 was repeated except that the hydrogen flowrate was increased to 30 cc/minute. Organic product analysis using conventional gas chromatography indicated that the starting material conversion was essentially complete. The hydrogen-containing products included 24.8% 2,2-dihydrohexafluoropropane (HFC-236fa), 54.6% 2-chloro-2-hydrohexafluoropropane (HCFC-226da) and 19.8% 1,2,2-trihydropentafluoropropane (HFC-235fa) and small quantities of other compounds.

This comparative experiment illustrates that when using palladium supported on acid-washed carbon as catalyst for the hydrogenolysis of CFC-216aa (where two chlorines of the starting compound are on the middle carbon and the two adjacent carbons contain trifluoromethyl groups) an olefin and/or a saturated product containing one less fluorine than the starting compound can be produced in significant amounts.

What is claimed is:

1. A process for the hydrogenolysis of 2,2-dichlorohexafluoropropane to 2,2-dihydrohexafluoropropane and 2-chloro-2-hydrohexafluoropropane which comprises reacting said starting material with at least 0.5 moles of hydrogen per mole of $CF_3CCl_2CF_3$ at a temperature of from about 100° C. to 250° C. in the presence of a catalyst containing a catalytically effective amount of palladium supported on a support selected from the group consisting of fluorinated alumina, aluminum fluoride and mixtures thereof to produce a three-carbon hydrogenolysis product from the hydrogenolysis of $CF_3CCl_2CF_3$ that contains at least 90% of the fluorine atoms contained in the $CF_3CCl_2CF_3$ reacted; wherein less than 5 mole percent of said product contains 5 fluorine substituents.

2. The process of claim 1 wherein the catalyst consists essentially of palladium on an aluminum fluoride support.

3. The process of claim 2 wherein the concentration of palladium on the support is within the range of from 0.1 to 10% by weight of the catalyst.

4. The process of claim 1 wherein $CF_3CCl_2CF_3$ is reacted with hydrogen until the conversion rate of $CF_3CCl_2CF_3$ decreases by at least about 20 percent compared to the conversion rate of $CF_3CCl_2CF_3$ using fresh catalyst at the same operating conditions; and wherein the catalyst is regenerated.

5. The process of claim 4 wherein the catalyst consists essentially of palladium on an aluminum fluoride or fluorinated alumina support; and wherein the concentration of palladium on said support is within the range of from 0.1 to 10% by weight of the catalyst.

6. The process of claim 1 wherein at least a stoichiometric amount of hydrogen is used.

7. The process of claim 1 wherein excess hydrogen is used.

8. A process for producing 2,2-dihydrohexafluoropropane and optionally, 2-hydroheptafluoropropane, comprising:

(a) reacting 2,2-dichlorohexafluoropropane with at least 0.5 moles of hydrogen per mole of 2,2-dichlorohexafluoropropane at a temperature of from about 100° C. to 250° C. in the presence of a catalyst containing a catalytically effective amount of palladium supported on a support selected from the group consisting of fluorinated alumina, aluminum fluoride and mixtures thereof to produce a hydrogenolysis product comprising 2,2-dihydrohexafluoropropane and 2-chloro-2-hydrohexafluoropropane; and (b) either (i) recycling the 2-chloro-2-hydrohexafluoropropane to produce additional 2,2-dihydrohexafluoropropane or (ii) producing 2-hydroheptafluoropropane from said 2-chloro-2-hydrohexafluoropropane.

9. The process of claim 8 wherein at least a stoichiometric amount of hydrogen is used.

10. The process of claim 8 wherein excess hydrogen is used.

11. The process of claim 8 wherein the catalyst consists essentially of palladium on an aluminum fluoride support.

12. The process of claim 11 wherein the concentration of palladium on the support is within the range of from 0.1 to 10% by weight of the catalyst.

13. The process of claim 8 wherein the three-carbon hydogenolysis product from the hydrogenolysis of $CF_3CCl_2CF_3$ contains at least 90% of the fluorine atoms contained in the $CF_3CCl_2CF_3$ reacted and less than 5 mole percent of said product contains 5 fluorine substituents.

14. The process of claim 8 wherein the catalyst consists essentially of palladium on a fluorinated alumina support; and wherein the concentration of palladium on the support is within the range of from 0.1 to 10% by weight of the catalyst.

15. The process of claim 8 wherein the starting material is reacted with hydrogen at a temperature of 200° C., or less.

16. The process of claim 8 wherein the starting material is reacted with hydrogen at a temperature of 150° C.

17. The process of claim 8 wherein $CF_3CCl_2CF_3$ is reacted with hydrogen until the conversion rate of $CF_3CCl_2CF_3$ decreases by at least about 20 percent compared to the conversion rate of $CF_3CCl_2CF_3$ using fresh catalyst at the same operating conditions; and wherein the catalyst is regenerated.

18. The process of claim 1 wherein the catalyst consists essentially of palladium on a fluorinated alumina support; and wherein the concentration of palladium on the support is within the range of from 0.1 to 10% by weight of the catalyst.

19. The process of claim 1 wherein the starting material is reacted with hydrogen at a temperature of 200° C., or less.

20. The process of claim 1 wherein the starting material is reacted with hydrogen at a temperature of 150° C.

* * * * *